United States Patent [19]

Boelsterli et al.

[11] Patent Number: 5,643,870

[45] Date of Patent: Jul. 1, 1997

[54] O-ACYLATED CYCLOSPORINS

[75] Inventors: Johann Jakob Boelsterli, Buus; Marcel Karl Eberle, Riehen; Reto Naef, Rheinfelden; Trevor Glyn Payne, Berne, all of Switzerland

[73] Assignee: Sandoz Ltd., Basel, Switzerland

[21] Appl. No.: 23,525

[22] Filed: Feb. 26, 1993

[30] Foreign Application Priority Data

Mar. 2, 1992 [GB] United Kingdom ............... 9204466

[51] Int. Cl.⁶ .................. C07K 7/06; C07K 5/12; A61K 38/00
[52] U.S. Cl. .................. 514/11; 514/9; 530/317
[58] Field of Search ................ 530/317

[56] References Cited

U.S. PATENT DOCUMENTS

| | | | |
|---|---|---|---|
| 4,220,641 | 9/1980 | Traber et al. | 530/317 |
| 4,649,047 | 3/1987 | Kaswan | 514/11 |
| 4,703,033 | 10/1987 | Seebach | 530/317 |
| 4,764,503 | 8/1988 | Wenger | 530/317 |
| 4,798,823 | 1/1989 | Witzel | 530/317 |
| 4,839,342 | 6/1989 | Kaswan | 514/11 |
| 4,996,193 | 2/1991 | Hewitt et al. | 514/11 |
| 5,202,310 | 4/1993 | Levy et al. | 530/317 |

FOREIGN PATENT DOCUMENTS

| | | |
|---|---|---|
| 0283801 | 9/1988 | European Pat. Off. . |
| 0296122 | 12/1988 | European Pat. Off. . |
| 0414632A2 | 2/1991 | European Pat. Off. . |
| 0484281 A2 | 5/1992 | European Pat. Off. . |
| 2205317 | 12/1988 | United Kingdom . |
| WO9006763 | 6/1990 | WIPO . |

OTHER PUBLICATIONS

V.F.J. Qüesniaux, et al.–Int. J. of Peptide Protein Res. 31, 1988 –pp. 173–185.
V.F.J. Quesniaux, et al.–Eur. J. Immol. 1987. pp. 1359–1365.
Heitman: Lancet, 339 873 (1992).
Lock et al.: Eur. Resp. J., 6(Supply. 17), 586s, p. 1873 (1993).
Herzog et al.: J. Autoimmunity, 5(Supp. A), xxxviii 286 (1982) and Szczeklik et al.: Loc. cit. 287 (1992).
Alexander et al.: Lancet, 339, 324–328 (1992).
Makino et al.: J. Allergy and Clin. Immunol., 93 (1/Pt 2), 260, Abs 583 (1984).
Alexander et al.: Amer. Rev. Resp.Dis. vol. 143 (Suppl.) No. 4/Part 2, p. A633 (1991).
Alexander et al.: Thorax vol. 46, p. 745P (1991).

*Primary Examiner*—Cecilia Tsang
*Assistant Examiner*—S. G. Marshall
*Attorney, Agent, or Firm*—Robert S. Honor; Melvyn M. Kassenoff; Thomas O. McGovern

[57] ABSTRACT

A cyclosporin of the formula

```
┌─ A—B—Sar—MeLeu—Val—MeLeu—
│
│                    Ala—Q—MeLeu—MeLeu—MeVal ─┐
└───────────────────────────────────────────────┘
``` wherein A is a residue of the formula

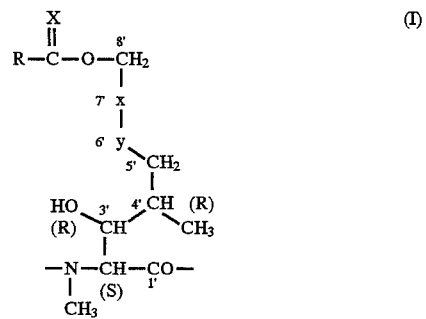

(I)

wherein
R is hydrogen, $C_{1-3}$alkyl, $C_{1-3}$ alkoxy or $C_{1-3}$alkylthio; halo-substituted-$C_{1-3}$alkyl, -$C_{1-3}$alkoxy or -$C_{1-3}$alkylthio; hydroxy-substituted-$C_{1-3}$alkyl, -$C_{2-3}$alkoxy or -$C_{2-3}$alkylthio; or amino or mono- or di-($C_{1-2}$alkyl)-amino,
X is oxygen or sulphur,
—x—y— is —CH=CH— (trans) or —CH₂—CH₂—,
B is -αAbu-, -Val-, -Thr- or -Nva- and
Q is -(D)Ala-; -(D)Ser-; -[O-(2-hydroxyethyl)(D)Ser]-; or -[O-acyl(D)Ser]- or -[O-(2-acyloxy ethyl)(D)Ser]-
in which the acyl residue is physiologically hydrolysable and acceptable, are useful in the topical treatment of asthma.

11 Claims, No Drawings

O-ACYLATED CYCLOSPORINS

The present invention relates to novel cyclosporins, their use as pharmaceuticals and pharmaceutical compositions comprising them, as well as to processes for their production.

The cyclosporins comprise a class of structurally distinctive, cyclic, poly-N-methylated undecapeptides, commonly possessing pharmacological, in particular immunosuppressive, anti-inflammatory or antiparasitic activity or activity in reversing or ameliorating resistance e.g. of tumours, to other drug therapy, in particular multi-drug resistance. The first of the cyclosporins to be isolated was the naturally occurring fungal metabolite Ciclosporin or Cyclosporine, also known as cyclosporin A and commercially available under the Registered Trademark SANDIMMUN® or SANDIMMUNE®. Ciclosporin is the cyclosporin of formula A.

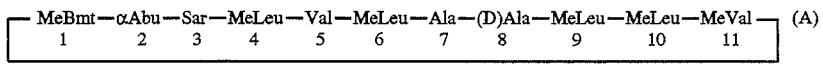

where -MeBmt- represents the N-methyl-(4R)-4-but-2E-en-1-yl-4-methyl-(L)threonine residue of formula B

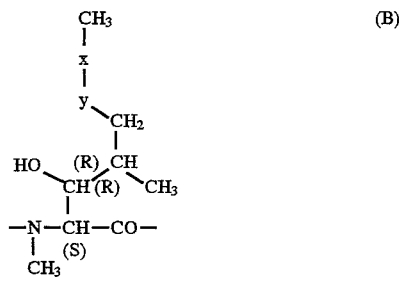

in which —x—y— is —CH=CH— (trans).

Since the original discovery of Ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf. Traber et al; 1, Helv. Chim. Acta, 60, 1247–1255 (1977); Traber et al; 2, Helv. Chim. Acta, 65, 1655–1667 (1982); Kobel et al, Europ. J. Applied Microbiology and Biotechnology, 14, 273–240 1982); and von Wartburg et al, Progress in Allergy, 38, 28–45, 1986)], as well as various non-natural cyclosporin derivatives and artificial or synthetic cyclosporins including dihydro-cyclosporins [in which the moiety —x—y— of the -MeBmt- residue (formula B above) is saturated to give —x—y—= —CH$_2$—CH$_2$—]; derivatised cyclosporins (e.g. in which the 3'-O-atom of the -MeBmt- residue is acylated or a further substituent is introduced at the α-carbon atom of the sarcosyl residue at the 3-position); and cyclosporins in which variant amino acids are incorporated at specific positions within the peptide sequence, e.g. employing the total synthetic method for the production of cyclosporins developed by R. Wenger—see e.g. Traber et al. 1, Traber et al, 2 and Kobel et al., loc. cit.; U.S. Pat. Nos. 4,108,985, 4,220,641, 4,288,431, 4,554,351, 4,396,542 and 4,798,823 European Patent Publications Nos. 34,567A, 56,782A, 300,784A and 300,785A; International Patent Publication No. WO 86/02080 and UK Patent Publications Nos. 2,206,119 and 2,207,678; Wenger 1, Transpl. Proc., 15 Suppl. 1:2230 (1983); Wenger 2., Angew. Chem. Int. Ed. 24 77 (1985) and Wenger 3., Progress in the Chemistry of Organic Natural Products, 50, 123 (1986).

The class comprised by the cyclosporins is thus now very large and includes for example, [Thr]$^2$-, [Val]$^2$- [Nva]$^2$- and [Nva]$^2$-[Nva]$^5$-Ciclosporin (also known as cyclosporins C, D, G and M respectively), [3-O-acetyl-MeBmt]$^1$-Ciclosporin (also known as cyclosporin A acetate), [Dihydro-MeBmt]$^1$-[Val]$^2$-Ciclosporin (also known as dihydro-cyclosporin D), [(D)Ser]$^8$-Ciclosporin, [MeIle]$^{11}$-Ciclosporin, [(D)MeVal]$^{11}$-Ciclosporin (also known as cyclosporin H), [MeAla]$^6$-Ciclosporin, [(D)Pro]$^3$-Ciclosporin and so on.

In accordance with conventional nomenclature for cyclosporins, these are defined throughout the present specification and claims by reference to the structure of Ciclosporin (i.e. cyclosporin A). This is done by first indicating those residues in the molecule which differ from those present in Ciclosporin and then applying the term "Ciclosporin" to characterise the remaining residues which are identical to those present in Ciclosporin. Thus [DihydroMeBmt]$^1$-[Val]$^2$-Ciclosporin is the cyclosporin having the sequence shown in Formula A but in which the -MeBmt- residue at position 1 is replaced by -dihydroMeBmt- (the residue of formula B above, wherein —x—y— is —CH$_2$—CH$_2$—) and -αAbu- at the 2-position is replaced by -Val-.

In addition, amino acid residues referred to by abbreviation, e.g. -Ala-, -MeVal-, -αAbu- etc. are, in accordance with conventional practice, to be understood as having the (L)-configuration unless otherwise indicated, e.g. as in the case of "-(D)Ala-". Residue abbreviations preceded by "Me" as in the case of "-MeLeu-", represent α-N-methylated residues. Individual residues of the cyclosporin molecule are numbered, as in the art, clockwise and starting with the residue -MeBmt-, -dihydro-MeBmt- or residue corresponding thereto in position 1. The same numerical sequence is employed throughout the present specification and claims.

The present invention relates to novel cyclosporins particularly useful for topical application e.g. in the treatment of diseases or conditions of the lung.

More particularly the present invention provides a cyclosporin wherein the residue at the 1-position is a residue of formula I

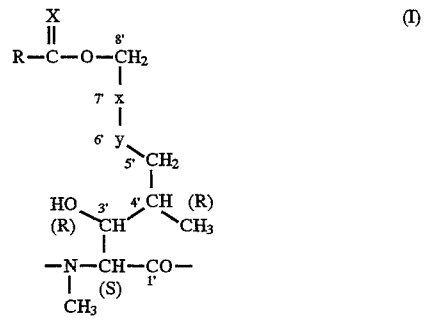

wherein

R is hydrogen, C$_{1-3}$alkyl, C$_{1-3}$alkoxy or C$_{1-3}$alkylthio; halo-substituted-C$_{1-3}$alkyl, -C$_{1-3}$alkoxy or -C$_{1-3}$alkylthio; hydroxy-substituted-C$_{1-3}$alkyl, -C$_{2-3}$alkyloxy or -C$_{2-3}$alkylthio; or amino or mono- or di-(C$_{1-2}$alkyl)-amino, X is oxygen or sulfur and —x—y— is —CH=CH— (trans) or —CH$_2$—CH$_2$—.

Preferred cyclosporins of the present invention are those of the formula II

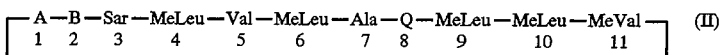 (II)

wherein

A is a residue of formula I as defined above,

B is -αAbu-, -Val-, -Thr- or -Nva- and

Q is -(D)Ala-, -(D)Ser- or -[O-(2-hydroxyethyl)(D)Ser]-; or -[O-acyl(D)Ser]- or -[O-(2-acyloxyethyl) (D) Ser]- in which the acyl residue is physiologically hydrolysable and acceptable.

Preferred alkyl groups as R are methyl and ethyl. Preferred alkoxy and alkylthio groups as R are methoxy, ethoxy, methylthio and ethylthio. Halo-substituted means chloro-, bromo-, fluoro- or iodo-substituted. Halo-substituted groups as R may be mono-, di- or poly-halo-substituted. A suitable halo-substituted-$C_{1-3}$alkyl group as R is trifluoromethyl. Suitable hydroxy-substituted-$C_{1-3}$alkyl groups as R are hydroxymethyl and 1-hydroxyethyl. Suitable mono- and di-alkylamino groups as R are methylamino, dimethylamino, and methylethylamino, dimethylamino being preferred.

In an embodiment in accordance with the invention, R is hydrogen, $C_{1-2}$alkyl, $C_{1-2}$alkoxy, $C_{1-2}$alkylthio, trifluoromethyl, hydroxy-substituted-$C_{1-2}$alkyl, amino or mono- or di-($C_{1-2}$alkyl)-amino, especially hydrogen, $C_{1-2}$alkyl, $C_{1-2}$alkoxy, trifluoromethyl, hydroxy-substituted-$C_{1-2}$alkyl or dimethylamino. Preferably R is hydrogen, $C_{1-2}$alkyl, $C_{1-2}$alkoxy or $C_{1-2}$alkylthio, especially $C_{1-2}$alkyl or $C_{1-2}$alkoxy, most especially methyl or methoxy. Most preferably R is $C_{1-2}$alkoxy, especially methoxy.

X is preferably oxygen.

—x—y— is preferably —CH=CH— trans.

B is preferably -αAbu-.

The term "physiologically hydrolysable and acceptable" employed in the definition of Q, defines acyl residues which are cleavable under physiological conditions to yield an acid which is itself physiologically tolerable at dosages to be administered. Suitable acyl residues include benzoyl and salicyl as well as residues of formula R'-CX'- wherein R' has the meanings given above for R but excluding amino and mono- and di-($C_{1-2}$alkyl)-amino and X' is oxygen or sulfur.

A group of cyclosporins in accordance with the present invention thus comprises those of formula II as defined above wherein Q is -(D)Ala-, -(D)Ser-, -[O-(2-hydroxyethyl)(D)Ser]- or a residue of formula III

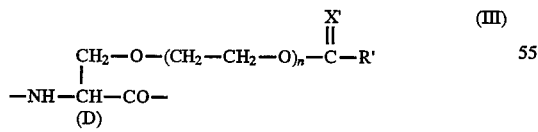 (III)

wherein n is zero or 1 and R' and X' have the meanings given above. When Q is a group of formula III, R' and X' in formula III will conveniently have the same meaning as R and X in formula I.

Suitably Q is -(D)Ala- or a group of formula III as defined above, especially -(D)Ala- or a group of formula III as defined above wherein n is zero. Preferably Q is -(D)-Ala-.

Cyclosporins of the invention wherein R and/or R' is asymmetric, for example in which R is α-hydroxyethyl, exhibit optical isomerism. In such cases individual isomers may be obtained in conventional manner, e.g. by synthesis from optically active starting materials (as in the case of examples 10 and 11 hereinafter) or by separation of initially obtained isomeric mixtures, for example employing chiral chromatographic techniques. Where such isomerism exists, the present invention is to be understood as embracing both individual isomeric forms, e.g. S- and R-enantiomers, as well as mixtures thereof, e.g. racemic and diastereomeric mixtures, unless otherwise specified. In general however, for pharmaceutical use in accordance with the present invention, use of individual enantiomers in pure or substantially pure form, e.g. comprising up to 95% or more pure single enantiomer, will be preferred.

The present invention also provides a process for the production of a cyclosporin as hereinbefore defined which process comprises a) for the production of a cyclosporin wherein the residue at the 1-position is a residue of formula I as hereinbefore defined said cyclosporin having a free hydroxy group, for example a cyclosporin of formula II as hereinbefore defined, wherein A is a residue of formula I as hereinbefore defined in which R is hydroxy-substituted-$C_{1-3}$alkyl, -$C_{1-3}$alkoxy or-$C_{1-3}$alkylthio and/or in which Q is -(D) Ser-, -[O-(2-hydroxyethyl)(D)Ser]- or a residue of formula III as hereinbefore defined in which R' is hydroxy-substituted-$C_{1-3}$alkyl, -$C_{1-3}$alkoxy or -$C_{1-3}$alkylthio, de-protecting a hydroxy-protected form thereof;

b) for the production of a cyclosporin wherein the residue at the 1-position is a residue of formula I as hereinbefore defined, for example a cyclosporin of formula II as hereinbefore defined, reacting a cyclosporin wherein the residue at the 1-position is a residue of formula IV

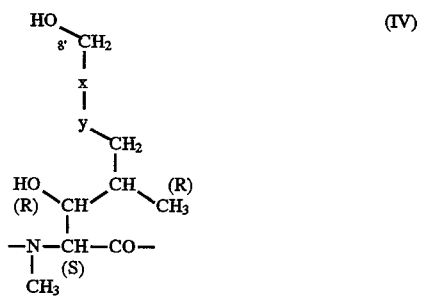 (IV)

wherein —x—y— has the meaning given for formula I, for example a cyclosporin of formula II as illustrated above wherein A is a residue of formula IV as hereinbefore defined above and B and Q have the meanings given for formula II, with a compound of formula V

 (V)

wherein Z is a leaving atom or group and R and X have the meanings given for formula I, whereby any hydroxy-substituted-$C_{1-3}$alkyl, -$C_{1-3}$alkoxy or -$C_{1-3}$alkylthio group as R is in hydroxy protected form and, when required, carrying out process step (a);

b) for the production of a cyclosporin of formula II as hereinbefore defined wherein Q is -[O-acyl (D) Ser]- or -[O-(2-acyloxyethyl) (D) Ser]- in which the acyl residue is physiologically hydrolysable and acceptable, acylating a cyclosporin of formula II as hereinbefore defined wherein Q is -(D) Ser- or -[O-(2-hydroxyethyl) (D)Ser]- with an appropriate acylating agent, for example by reaction with a compound of formula (V')

wherein R' and X' have the meanings hereinbefore given for formula III, whereby any hydroxy-substituted-$C_{1-3}$alkyl, -$C_{13}$alkoxy or -$C_{1-3}$alkylthio group as R' is in hydroxy protected form and Z is a leaving atom or group and, when required, carrying out process step (a);

and recovering the cyclosporin thus obtained.

Suitable protecting groups in relation to process step (a) include t.butylsilyl. Deprotection in accordance with step (a) may be effected by conventional procedures for example using tetrabutylammonium fluoride in accordance with the procedures described in Corey et al., J.Am. Chem. Soc., 94, 6190 (1972).

Suitable compounds V and V' for use in relation to process steps (b) and (c) include acyl- and thioacyl-halides (e.g. in which Z=chlorine or bromine) and -anhydrides (i.e. in which Z=R-CX-O- or R'-CX'-O-). Reaction is suitably performed in the presence of an acid binding agent, for example, 4-dimethylaminopyridine at temperatures of from ca. $-20°$ to $+60°$ C.

In the cyclosporin starting materials for the above procedures, 8'-hydroxy groups of the 1-position residue (formula IV) are more reactive than hydroxy groups which may be present at the 8-position residue, e.g. when Q is -(D)Ser-. By process step (b) it is accordingly possible to introduce a group R-CX- preferentially at the 1-position residue, i.e. using 1 equivalent of formula V compound. This may be followed by reaction step (c) to introduce a different group R'-CX'- at the 8-position residue. Where it is desired to introduce a group R'-CX'- at the 8-position which is identical to the group R-CX- at the 1-position, steps (a) and (b) may be carried out in a single reaction employing two equivalents of the (same) formula V/V' compound.

Starting materials of formulae V and V' are known or may be prepared analogously to the known materials. Hydroxy-substituted acyl halides in O-t.butyl silyl protected form are for example described in Chemical Abstracts 109-149284 and Bischofsberger et al., J.Org. Chem., 53, 3457 (1988).

Cyclosporin starting materials required for process step (b) may be prepared in accordance with the following reaction sequence. (In this reaction sequence, only the 1-position residue of the cyclosporin molecule is represented in detail. The remainder of the molecule is indicated as "(rs2-11)", this representing in relation to e.g. formula II above, the residue sequence 2 to 11 as shown in and defined for formula II. —x—y— has the meaning given for formula I.)

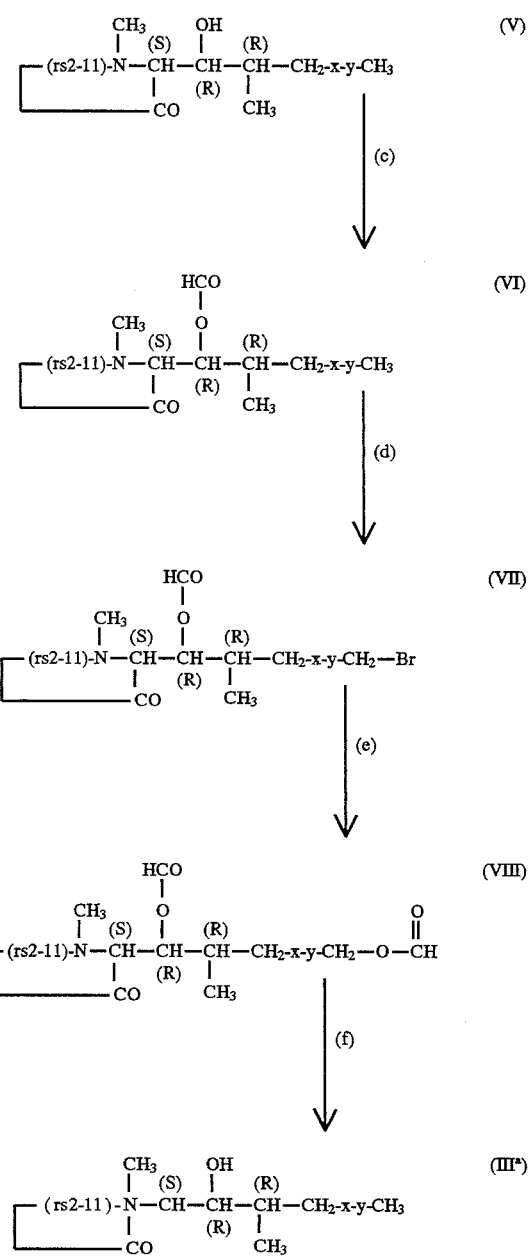

Steps (c) through (f) are suitably performed in accordance with the general procedures hereinafter described in example 1 or analogously thereto. When the 8-position residue of (rs2–11) (i.e., in relation to formula II, the residue Q, is -(D)Ser- or -[O-(2-hydroxyethyl)(D)Ser]- the free hydroxy group thereof will also undergo formylation at step (c) and subsequent deformylation at step (f).

Cyclosporin starting materials of formula V are known or may be produced analogously to the known cyclosporins. Thus when (rs2–11) represents the sequence 2 through 11 of formula II, in which B has the meaning given for formula II and Q is -(D)Ala- the cyclosporins defined are cyclosporins and dihydrocyclosporins A, C, D and G. Corresponding cyclosporins wherein Q is -(D)Ser- or -[O-acyl(D)Ser]- are described for example in European Patent Publication 56782 A and UK Patent specification 2 155 936 A. Corresponding cyclosporins wherein Q is -[O-(2-hydroxyethyl)(D) Ser]- or -[O-(2-acyloxyethyl)(D)-Ser]- are described for example in European Patent Publication 414632 (=Application No. P0810567.9).

The cyclosporin of formula II as illustrated above in which A is a residue of formula IV as illustrated above in which —x—y— is —CH=CH— (trans), in which B is -αAbu- and Q is -(D)Ala- is also known as a metabolite of cyclosporin A. It is the metabolite designated in the art as M17.

The following examples are illustrative of the processes for the production of cyclosporins of the invention.

EXAMPLE 1

Production of [(8'-Methoxycarbonyloxy)MeBmt]$^1$-Ciclosporin

[Formula II:A=a residue of formula I in which R=CH$_3$O-, X=O and —x—y—=—CH=CH—(trans; B=-αAbu-; Q=-(D)Ala-] Process step (a).

0.33 ml of chloromethylformate are added to a solution of 4.9 g [(8'-hydroxy)MeBmt]$^1$-Ciclosporin and 1.9 g 4-dimethylaminopyridine in 50 ml dimethylformamide under anhydrous conditions. The reaction mixture is stirred for 18 hrs at room temperature and the solvent removed under reduced pressure. The residue is taken up in ethyl acetate, washed with aqueous tartaric acid and aqueous Na$_2$CO$_3$, the solvent removed under reduced pressure and the residue chromatographed on silica gel using ethyl acetate saturated with water, to yield the title product: $[\alpha]_D^{20}$=-151.8° (c=2 in CHCl$_3$), r$_F$=0.57 (ethyl acetate saturated with H$_2$O:SiO$_2$].

The starting material may be produced as follows:
Process Step (c)
Production of [(3'-O-formyl)MeBmt]$^1$-Ciclosporin [=Formula VI].

15 ml acetyl formate are added to a solution of 9.6 g Ciclosporin (cyclosporin A) and 3.9 g 4-dimethylaminopyridine in 100 ml acetone, over a period of 30 mins. at room temperature. The reaction mixture is stirred for 20 hrs. at room temperature and the solvent removed under reduced pressure. The residue is taken up in ethyl acetate, washed with aqueous Na$_2$SO$_4$ and the organic solvent removed under reduced pressure. The residue is crystallised from boiling hexane to yield the title product: m.p.=195°–197° C.

Process Step (d)
Production of [(8'-Bromo-3'-O-formyl)MeBmt]$^1$-Ciclosporin [=Formula VII].

75 g of the product of step (c), 11.7 g N-bromosuccinimide and 1 g azoisobutyronitrile in suspension in 750 ml CCl$_4$ are heated under reflux for 2 hrs. The residue is filtered, washed with aqueous NaHCO$_3$, aqueous tartaric acid and brine and the organic lager dried over Na$_2$SO$_4$. The solvent is removed under reduced pressure to yield the title compound which is reacted further without additional purification.

Process step (e)
Production of [(3'-O-formyl-8'-formyloxy)MeBmt]$^1$-Ciclosporin [Formula VIII]

86 g of the product of step (d), 1 g NaI and 27 g tetraethylammonium formate in 750 ml methyl ethyl ketone are heated under reflux for 4 hrs. The solvent is removed under reduced pressure, the residue taken up in ethyl acetate and washed with aqueous Na$_2$CO$_3$, aqueous tartaric acid and brine. The organic layer is dried over Na$_2$SO$_4$ and the solvent removed under reduced pressure to yield the title product which is reacted further without additional purification.

Process step (f)
Production of [(8'-Hydroxy)MeBmt]$^1$-Ciclosporin [=M 17]

71 g of the product of step (e) is stirred for 18 hrs. at room temperature in 0.8M ethanolic methylamine. The solvent is removed under reduced pressure and the residue chromatographed on silica gel using ethyl acetate saturated with H$_2$O. Removal of the solvent under reduced pressure yields the title product as a white foam r$_F$=0.31 (ethyl acetate saturated with H$_2$O:silica).

The following cyclosporins of formula II as illustrated above in which A is a residue of formula Ia

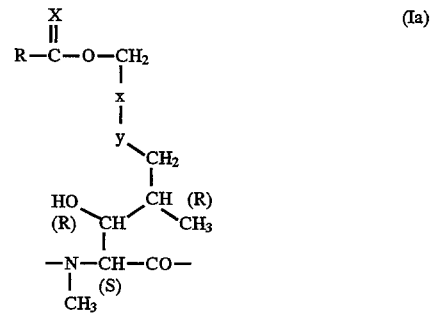

(Ia)

in which R and —x—y— have the meanings given below, B is -αAbu- and Q is -(D)Ala- may be prepared analogously:

| EXAMPLE | R | -x-y- | $[\alpha]_D^{20}$ |
|---|---|---|---|
| 2 | H | —CH=CH— (trans) | -183.4° (c = 0.5 in CH$_3$OH) |
| 3 | CH$_3$— | —CH=CH— (trans) | -148° (c = 2 in CH$_3$OH) |
| 4 | CH$_3$— | —CH$_2$—CH$_2$— | -235° (c = 1.04 in CHCl$_3$) |
| 5 | C$_2$H$_5$— | —CH=CH— (trans) | -214.85° (c = 1.03 in CHCl$_3$) |
| 6 | C$_2$H$_5$O— | —CH=CH— (trans) | -174.8° (c = 0.5 in CH$_3$OH) |
| 7 | CF$_3$— | —CH=CH— (trans) | -177.1° (c = 0.5 in CH$_3$OH) |
| 8 | (CH$_3$)$_2$N— | —CH=CH— (trans) | -168.7° (c = 0.5 in CH$_3$OH) |
| 9* | HO—CH$_2$— | —CH=CH— (trans) | -181.5° (c = 0.5 in CH$_3$OH) |

-continued

| EXAMPLE | R | -x-y- | $[\alpha]_D^{20}$ |
|---|---|---|---|
| 10* | HO—CH—<br>\|<br>CH₃ | —CH=CH— (trans) | −178.9° (c = 0.5 in CH₃OH) |
| 11* | HO—CH—<br>\|<br>CH₃ | —CH=CH— (trans) | −175.7° (c = 0.5 in CH₃OH) |

*Production process entails initial reaction with (CH₃)₃C—Si—O—CH₂COCl/(CH₃)₃C—Si—O—CH(CH₃)COCl followed by deprotection with tetrabutylammoniumfluoride according to the procedures of Corey et al. J. Am. Chem. Soc. 94, 6190 (1972).

The following cyclosporins of formula II as illustrated above wherein A is a residue of formula Ia as illustrated above in which R has the meanings given in the table below and —x—y— is —CH=CH— (trans), B is -αAbu- and Q is a residue of formula IIIa

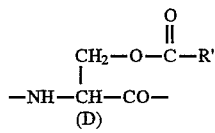

in which R' has the meaning given in the table below, may also be prepared analogously but employing 2 equivalents of the required acylating agent.

| EXAMPLE | R | R' | $[\alpha]_D^{20}$ = |
|---|---|---|---|
| 12 | CH₃— | CH₃— | −170.9 (c = 0.5 in CH₃OH) |
| 13 | CH₃O— | CH₃O— | −161.5 (c = 0.5 in CH₃OH) |

The cyclosporins of the present invention have potent immunosuppressive and anti-inflammatory activity. In particular they inhibit antigen-induced inflammatory cell infiltration, for example into the airways. In vivo this activity is apparent following topical administration, e.g. following topical administration to the airways via the pulmonary route. The cyclosporins of the invention are in contrast found to possess substantially reduced, or to be substantially devoid of, activity, e.g. anti-inflammatory or immunosuppressive activity, in vivo when administered systemically, for example following oral administration.

The immunosuppressive and anti-inflammatory properties of cyclosporins of the invention may be demonstrated in standard test models in vitro and in vivo, e.g. as follows:

1. Immunosuppressive Activity (in vitro)

1.1 Murine Mixed Lymphocyte Reaction

Ca. 0.5×10⁶ lymphocytes from the spleen of female (8–10 weeks) Balb/c mice are incubated for 5 days in 0.2 ml cell growth medium with ca. 0.5×10⁶ lymphocytes from the spleen of female (8–10 weeks) CBA mice. Test substance is added to the medium at various concentrations. Activity is assessed by ability to suppress proliferation associated DNA synthesis as determined by incorporation of radiolabelled thymidine.

Cyclosporins in accordance with the present invention inhibit thymidine incorporation at concentrations of the order of from 0.005 to 0.025 μg/ml.

1.2 Mishell-Dutton Test

Ca. 10⁷ lymphocytes from the spleen of OFI, female mice are co-cultured with ca. 3×10⁷ sheep erythrocytes for 3 days. Test substance is added to the incubation medium in varying concentrations. Lymphocytes are harvested and plated onto agar with fresh sheep erythrocytes as antigen. Sensitised lymphocytes secrete antibody that coats the erythrocytes, which lyse to form a plaque in the presence of complement. Activity is assessed by reduction in the number of plaque forming, i.e. antibody producing, cells. Cyclosporins in accordance with the present invention reduce the numbers of plaque forming cells at concentrations of the order of from 0.03 to 0.05 μg/ml.

2. Influence on Allergen-Induced Pulmonary Eosinophilia (in vitro)

Male Himalayan spotted guinea pigs (300 g, BRL) are sensitised to ovalbumin (OA) by i.p. injection of 1 ml of a suspension of OA (10 μg) with Al(OH)₃ (100 mg) and B-pertussis vaccine (0.25 ml) in saline (0.9% w/v). For oral studies the procedure is repeated 1× after 2 weeks and the animals are used one week later. For inhalation studies the procedure is repeated 2× at 3 week intervals and the animals are used one week after the last injection.

Challenge is effected employing a saline solution of OA, nebulized for discharge into an exposure chamber. Test animals are exposed to OA by nose-only inhalation for 60 minutes. For oral studies OA solution is used at a concentration of 0.05%. For inhalation studies OA solution is used at a concentration of 0.01%.

Test substance is administered (a) orally and (b) by inhalation. For oral studies test substance is administered p.o. in olive oil 1× daily for 3 days or in powder form in methylcellulose once prior to OA challenge. On day 3 test animals receive test substance 1.5 hrs. prior to and 6 hrs. after OA challenge. For inhalation studies, test substance is micronised for delivery to test animals restrained within a flow-past, nose-only inhalation chamber. Administration by inhalation is effected 15 mins. prior to OA challenge.

Efficacy of administered test substance is determined by bronchoalveolar lavage (BAL) and cell counting. For this purpose animals are sacrificed with Na pento-barbitone (100 mg/kg i.p.) and the trachea is exposed and cannulated. 5 successive 10 ml aliquots of Ca²⁺ and Mg²⁺ free Hank's balanced salt solution (HBSS), containing bovine serum albumin (BSA, 0.3%), EDTA (10 mM) and HEPES (10 mM) is then introduced into the lung and immediately aspirated by gentle compression of the lung tissue. Total cell counts in pooled eluates are determined using an automatic cell counter. Lavage fluid is centrifuged at 200 g for 10 minutes and the cell pellet resuspended in 1 ml of supplemented HBSS. 10 μl of the cell suspension is added to 190 μl of Turk's solution (1:20 dilution). Differential cell counts are made from smears stained by Diff-Quick. Cells are identified and counted under oil immersion (×1,000). A minimum of 500 cells per smear are counted and the total population of each cell type is calculated.

In untreated animals OA challenge induces increase of all cell types in BAL fluid 24 hours after challenge. Prior administration of cyclosporins in accordance with the present invention by inhalation at dosages of the order of from 1.0 to 15.0 mg/kg reduces eosinophil count in BAL in a dose dependent manner as compared with untreated controls. Cell counts for other leucocytes (macrophages, neutrophils) are also reduced. In contrast, repeated oral administration of cyclosporin in accordance with the present invention has substantially no influence on cell count as compared with untreated controls.

Cyclosporins of the invention are accordingly useful for the treatment of diseases or conditions responsive to or requiring topical anti-inflammatory, immunosuppressive or related therapy, e.g. for topical administration for the treatment of such diseases or conditions of the eye, nasal passages, buccal cavity, skin, colon or, especially, airways or lung. In particular cyclosporins of the invention permit topical anti-inflammatory, immunosuppressive or related therapy with the concomitant avoidance or reduction of undesirable systemic side-effect, for example general systemic immunosuppression.

Cyclosporins of the invention are in particular useful for the treatment of diseases and conditions of the airways or lung, in particular inflammatory or obstructive airways disease. They are especially useful for the treatment of diseases or conditions of the airways or lung associated with or characterised by inflammatory cell infiltration or other inflammatory event accompanied by inflammatory cell, e.g. eosinophil and/or neutrophil, accumulation. They are most especially useful for the treatment of asthma.

Cyclosporins of the invention are useful in the treatment of asthma of whatever type or genesis including both intrinsic and, especially, extrinsic asthma. They are useful for the treatment of atopic or non-atopic asthma, including allergic asthma, bronchitic asthma, excercise induced asthma, occupational asthma, asthma induced following bacterial infection and other non-allergic asthmas. Treatment of asthma is also to be understood as embracing treatment of "wheezy-infant syndrome", that is treatment of subjects, e.g. of less that 4 or 5 years of age, exhibiting wheezing symptoms, in particular at night, and diagnosed or diagnosable as "wheezy infants", an established patient category of major medical concern and now more correctly identified as incipient or early-phase asthmatics. Cyclosporins of the invention are in particular useful for the treatment of asthma in subjects whose asthmatic status is either steroid dependent or steroid resistant.

Cyclosporins of the invention are also useful for the treatment of bronchitis or for the treatment of chronic or acute airways obstruction associated therewith. Cyclosporins of the invention may be used for the treatment of bronchitis of whatever type or genesis, including, for example, acute bronchitis, arachidic bronchitis, catarrhal bronchitis, chronic bronchitis, croupous bronchitis, phthinoid bronchitis and so forth.

Cyclosporins of the invention are in addition useful for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis and, in particular, byssinosis.

Cyclosporins of the invention may also be used for the treatment of eosinophil-related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

The word "treatment" as used above in relation to the treatment of diseases of the airways and lungs, in particular asthma, is to be understood as embracing both symptomatic and prophylactic modes, that is the immediate treatment, e.g. of acute inflammation (symptomatic treatment) as well as advance treatment to prevent, ameliorate or restrict long term symptomatology (prophylactic treatment). The term "treatment" as used in the present specification and claims in relation to such diseases is to be interpreted accordingly as including both symptomatic and prophylactic treatment, e.g. in the case of asthma, symptomatic treatment to ameliorate acute inflammatory event and prophylactic treatment to restrict on-going inflammatory status and to ameliorate future bronchial exacerbation associated therewith.

Cyclosporins of the invention may also be used to treat any disease or condition of the airways or lung requiring immunosuppressive therapy, e.g. for the treatment of autoimmune diseases of, or as they affect, the lungs (for example, for the treatment of sarcoidosis, alveolitis or chronic hypersensitivity pneumonitis) or for the maintainance of allogenic lung transplant, e.g. following lung or heart lung transplantation.

As previously indicated, for the above purposes, cyclosporins of the invention will be administered topically within the airways, e.g. by the pulmonary route/by inhalation. As also previously noted, while having potent efficacy when administered topically, cyclosporins of the invention are devoid of, or exhibit relatively reduced, systemic activity, e.g. following oral administration. Cyclosporins of the invention thus provide a means for the treatment of diseases and conditions of the airways or lung, e.g. as hereinabove set forth, with the avoidance of unwanted systemic side effect, e.g. consequent to inadvertant swallowing of drug substance during inhalation therapy. (It is estimated that during the course of manoeuvres required to effect administration by inhalation, up to 90% or more of total drug substance administered will normally be swallowed rather than inhaled.)

By the provision of cyclosporins which are topically active, e.g. effective when inhaled, but systemically inactive the present invention makes cyclosporin therapy available to subjects for whom such therapy might otherwise be excluded, e.g. due to the risk of systemic, in particular immunosuppressive, side effect.

Cyclosporins of the invention are also useful for the treatment of other diseases or conditions, in particular diseases or conditions having an autoimmune or inflammatory component and for which topical therapy may be practiced, for example, treatment of diseases and conditions of the eye such as conjunctivitis, keratoconjunctivitis sicca, and vernal conjunctivitis and maintainance of corneal transplant, diseases affecting the nose including allergic rhinitis, diseases and conditions of the skin including psoriasis, atopic dermatitis, pemphigus and contact dermatitis, as well as diseases of the colon, for example Crohn's disease and ulcerative collitis.

For the above purposes, cyclosporins of the invention may be employed in any dosage form appropriate for topical administration to the desired site. Thus for the treatment of diseases of the airways or lungs cyclosporins of the invention may be administered via the pulmonary route/by inhalation from an appropriate dispenser device.

For this purpose cyclosporins of the invention may be employed in any suitable finely dispersed or finely dispersible form, capable of administration into the airways or lungs, for example in finely divided dry particulate form or in dispersion or solution in any appropriate (i.e. pulmonarily administerable) solid or liquid carier medium. For administration in dry particulate form, cyclosporins of the invention may, for example, be employed as such, i.e. in micronised form without any additive materials, in dilution with other appropriate finely divided inert solid carrier or diluent (e.g. glucose, lactose, mannitol, sorbitol, ribose, mannose or xylose), in coated particulate form or in any other appropriate form as known in the art for the pulmonary administration of finely divided solids.

Pulmonary administration may be effected using any appropriate system as known in the art for delivering drug substance in dry or liquid form by inhalation, e.g. an atomiser, nebulizer, dry-powder inhaler or like device. Preferably a metered delivery device, i.e. capable of delivering a pre-determined amount of cyclosporin at each actuation, will be employed. Such devices are known in the art.

For nasal administration, cyclosporins of the invention will suitably be administered in liquid form from a nasal applicator. Suitable topical forms for the treatment of diseases or conditions of the skin will include, for example, creams, gels, ointments, pastes, cataplasms, plasters, transdermal patches and the like. Formulations for dermal application will appropriately contain a skin penetration enhancer, e.g. as known in the art, for example azone. Forms suitable for ophthalmic use will include lotions, tinctures, gels, ointments and ophthalmic inserts, again as known in the art. For rectal administration, i.e. for topical therapy of the colon, cyclosporins of the invention may be administered in suppository or enema form, in particular in solution, e.g. in vegetable oil or like oily system for use as a retention enema.

The present invention accordingly further provides:
A. A method of treating a disease or condition requiring anti-inflammatory, immunosuppressive or related therapy in a subject in need thereof, which method comprises topically administering an effective amount of a cyclosporin of the invention; as well as
B. A cyclosporin of the invention for use as a pharmaceutical for example for use in treating a disease or condition requiring anti-inflammatory, immuno-suppressive or related therapy, e.g. for use in a method as defined under A above.

The method as defined under A above applies in particular to the treatment of diseases and conditions of the eye, nose, throat, buccal cavity, skin, colon or, especially, airways or lungs. It is applicable to any disease or condition as hereinbefore set forth, in particular to any disease or condition of the airways or lungs requiring anti-inflammatory or related therapy, especially any disease or condition of the airways or lungs characterised by inflammatory cell infiltration and, most especially for the treatment of asthma.

The present invention further provides:
C. A pharmaceutical composition for topical administration, i.e. in topically administerable form, comprising a cyclosporin of the invention together with pharmaceutically acceptable diluent or carrier or cyclosporin of the invention in a form or in a means or device enabling or facilitating topical administration.

Pharmaceutically acceptable diluents or carriers under D above are diluents or carriers acceptable for topical application at the intended side of therapy, e.g. diluents or carriers acceptable for topical administration pulmonarily, dermally, nasally, ocularly or rectally. Forms in topically administerable form, e.g. enabling or facilitating topical administration, include, e.g. dry powder preparations of the active ingredient (i.e. cyclosporin of the invention) in substantially pure form, for example as employed in the art for delivery from a dry powder inhalation device. Means or devices enabling or facilitating topical administration include, in particular, inhalation devices as well as containers and the like from which the active ingredient may be delivered in a form capable of topical application. Preferred embodiments as defined under C will be such as permit topical administration within the airways or lungs, e.g. by inhalation.

Dosages of cyclosporins of the invention employed in practicing the method of the present invention will of course vary depending on the site of treatment, the particular condition to be treated, the severity of the condition, the subject to be treated (e.g. in terms of body weight, age and so forth) as well as the effect desired. In general, for treating diseases or conditions of the airways or lungs, e.g. for use in treating inflammatory or obstructive airway disease, for example asthma, cyclosporins of the invention will suitably be administered topically to the airways or lungs, e.g. by inhalation, at dosages of the order of from 20 to 400 mg/day, e.g. from 50 or 100 to 300, e.g. from 200 to 300 mg/day. Dosages will appropriately be administered from a metered delivery system in a series of from 1 to 5 puffs at each administration, with administration performed once to four times daily. Dosages at each administration will thus conveniently be of the order of from about 5 to 100 mg, more suitably from 12.5 or 25 to 100 mg, e.g. administered with a metered delivery device, e.g. capable of delivering, e.g. 1 to 25 mg cyclosporin, per actuation.

For the treatment of diseases of the eye and nose cyclosporins of the invention will generally be administered in the form of an appropriate composition, e.g. eye drop, gel, collyrium or the like or nasal drop, nasal spray or the like, comprising from about 0.05 to about 10%, especially from about 0.05 to about 5%, more preferably from about 0.1 to about 2.5% cyclosporin by weight, in an ocularly or nasally applicable diluent or carrier for application to the surface of the eye or nasally in an amount of from about 0.05 to about 0.2 ml composition, e.g. from about 0.05 to about 0.1 ml composition, once or from two to three times daily.

For the treatment of diseases or conditions of the colon, in general suitable daily dosages of cyclosporins of the invention will be of the order of from about 0.5 to about 15.0, preferably from about 2.5 to about 10.0 mg/kg, suitably administered as a retention enema administered once or in divided doses 2×daily. Each administered dosage will thus suitably comprise from about 17.5 to about 1,000, preferably from about 35 to about 700, more preferably from about 87.5 to about 550 mg cyclosporin of the invention together with an appropriate rectally applicable diluent or carrier therefor. Suitable cyclosporin concentrations for use in such retention enema systems are of the order of from about 0.5 to about 12.0, preferably from about 1.0 to about 10.0, more preferably from about 2.0 to about 7.0 mg/ml.

For dermal administration for the treatment of diseases or conditions of the skin, cyclosporins of the invention will generally be administered in appropriate, i.e. dermally applicable, form comprising from ca. 1 to 10% by weight of cyclosporin together with a dermally acceptable diluent or carrier therefor. Such compositions will suitably be applied to the site of treatment in an amount of from ca. 0.005 to ca. 0.05 g/cm², 1, 2 or 3×daily.

The preferred cyclosporin of the present invention is the product of example 1 namely [(8'-methoxycarbonyloxy) MeBmt]¹-Ciclosporin. Specific results for this cyclosporin in one series of tests performed in accordance with the methods described under 1.1 to 1.3 and 2 above are as follows:

| TEST | RESULTS |
| --- | --- |
| 1.1 | IC50 = 0.015 µg/ml |
| 1.2 | IC50 = 0.043 µg/ml |
| 2. BY INHALATION | ID50 = ca. 4 mg/kg |
| 2. ORALLY | no inhibition of eosinophil accumulation at 100 mg/kg/day in oil 3× or at 320 mg/kg in methylcellulose 1×. |

We claim:
1. A cyclosporin of the formula

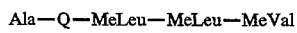

wherein A is

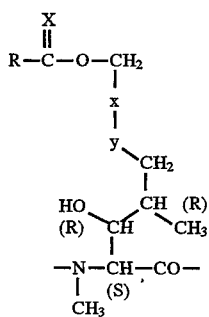

wherein
R is hydrogen, $C_{1-3}$alkyl, $C_{1-3}$alkoxy or $C_{1-3}$alkylthio; halo-substituted-$C_{1-3}$alkyl, -$C_{1-3}$alkoxy or -$C_{1-3}$alkylthio; hydroxy-substituted-$C_{1-3}$alkyl, -$C_{2-3}$alkoxy or -$C_{2-3}$alkylthio; amino or mono- or di-($C_{1-2}$alkyl)amino,
X is oxygen or sulphur,
—x—y— is —CH=CH— (trans) or —CH₂—CH₂—,
B is -αAbu-, -Val-, -Thr- or -Nva- and
Q is -(D)Ala-, -(D)Ser-[O-(2-hydroxyethyl) (D) Ser]-, or -[O-acyl(D)Ser]- or -[O-(2-acyloxethyl) (D) Ser]- in which the acyl group is physiologically hydrolyzable and acceptable.

2. A cyclosporin according to claim 1 wherein
R is methoxy, X is oxygen, —x—y— is —CH=CH— (trans),
B is -αAbu- and Q is -(D)Ala-.

3. A cyclosporin according to claim 1 wherein
X is oxygen, —x—y— is —CH=CH—(trans), B is -αAbu- and Q is -(D)Ala-, and R is hydrogen, methyl, ethyl, ethoxy, trifluoromethyl, dimethylamino, hydroxymethyl, [S]α-hydroxyethyl or [R]α-hydroxyethyl;

or wherein
X is oxygen, —x—y— is —CH₂—CH₂—, B is -αAbu-, Q is -(D)Ala- and R is methyl;

or wherein
X is oxygen, —x—y— is —CH=CH—(trans), B is -αAbu-, Q is

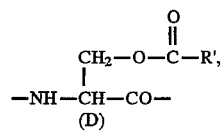

and R and R' are both methyl or both methoxy.

4. A pharmaceutical composition for topical administration comprising a cyclosporin as claimed in claim 1 together with a pharmaceutically acceptable diluent or carrier therefor.

5. A method of treating asthma in a subject in need of said treatment which comprises topically administering to said subject a therapeutically effective amount of a cyclosporin of claim 1.

6. A cyclosporin according to claim 1 wherein R is hydrogen, methyl, ethyl, methoxy, ethoxy, methylthio, ethylthio, trifluoromethyl, hydroxymethyl, 1-hydroxyethyl, methylamino, dimethylamino, or methylethylamino.

7. A cyclosporin according to claim 1 wherein R is hydrogen, methyl, ethyl, methoxy, ethoxy, trifluoromethyl, hydroxymethyl, 1-hydroxyethyl, or dimethylamino;
X is oxygen;
—x—y— is —CH=CH—(trans);
B is -αAbu-; and Q is -(D)Ala-, -(D)Ser-, -[O-(2-hydroxyethyl)-(D)Ser]-, or

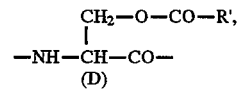

where R' has a significance of R excluding dimethylamino.

8. A cyclosporin according to claim 7, wherein Q is -(D)Ala- and R is hydrogen, methyl, or ethyl.

9. A cyclosporin according to claim 7, wherein Q is -(D Ala- and R is ethoxy.

10. A cyclosporin according to claim 7, wherein Q is -(D)Ala- and R is trifluoromethyl, hydroxymethyl, 1-hydroxyethyl, or dimethylamino.

11. A cyclosporin according to claim 7, wherein Q is

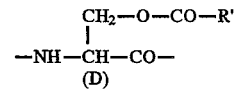

and R and R' are both methyl or methoxy.

* * * * *